United States Patent [19] [11] 4,144,760
Schlüeter et al. [45] Mar. 20, 1979

[54] METHOD AND IMPLEMENT TO TAKE AND COLLECT SAMPLE MATERIAL, ESPECIALLY FOR SCIENTIFIC OR DIAGNOSTIC EXAMINATION

[75] Inventors: Gert Schlüeter, Liederbach, Taunus; Wilhelm Schuster, Frankfurt am Main, both of Fed. Rep. of Germany

[73] Assignee: Battelle-Institut e.V., Frankfurt am Main, Fed. Rep. of Germany

[21] Appl. No.: 838,393

[22] Filed: Sep. 30, 1977

[30] Foreign Application Priority Data

Sep. 30, 1976 [DE] Fed. Rep. of Germany ....... 2644281

[51] Int. Cl.$^2$ ............................................. G01N 1/28
[52] U.S. Cl. .................................................... 73/425
[58] Field of Search ................ 73/425; 128/2 F, 2 W; 356/36

[56] References Cited

U.S. PATENT DOCUMENTS 4,059,404  11/1977  Schuster et al. .................... 128/2 W

FOREIGN PATENT DOCUMENTS 961209  1/1975  Canada .................................. 128/2 W

*Primary Examiner*—S. Clement Swisher
*Attorney, Agent, or Firm*—Virgil H. Marsh

[57] ABSTRACT

A method for taking and collecting sample material. A sampler is used which consists entirely, or at least at its surface or contact area, of a plastic material which is soluble in water. The sampler, after wetting and hence superficial dissolution, is brought into contact with the surface to be examined. The sample material sticks to the plastic. The sampler is removed and dissolved, whereby the sample material is collected.

10 Claims, No Drawings

METHOD AND IMPLEMENT TO TAKE AND COLLECT SAMPLE MATERIAL, ESPECIALLY FOR SCIENTIFIC OR DIAGNOSTIC EXAMINATION

BACKGROUND OF THIS INVENTION

1. Field of This Invention

This invention relates to a method and an implement for taking and collecting sample material, primarily for diagnostic or scientific examinations in biology, medicine or engineering.

2. Prior Art

Methods and implements are known for taking and collecting sample material, particularily for diagnostic and scientific examinations in biology, medicine and engineering. The range of samples taken and collected include samples of bacteria and other micro-organisms, of cellular materials and of other very small particles of organic or inorganic materials. So far, such samples have been taken primarily by means of spatulas, cotton swabs or sharp instruments. It is also common practice, e.g., in criminology, to take up minute particles by means of a plastic film coated with an adhesive and then to remove the particles mechanically from this film for further diagnosis or to leave them on the film and examine them together with the film. All of such methods have the disadvantage that damage to or destruction of the sample, loss of sample material, contamination by the carrier material and undesired selection processes cannot be avoided.

BROAD DESCRIPTION OF THIS INVENTION

An object of this invention is to provide a method whereby undamaged, unchanged and representative samples can be taken and evaluated. Another object of this invention is to provide a method whereby, when such samples are taken, damage to the sampling area is avoided. A further object of this invention is to provide an implement for taking and collecting such sample by such method. Still another object of this invention is to provide a method and an implement which avoid the disadvantages of the prior art. Other objects and advantages of this invention are set out herein or are obvious herefrom to one ordinarily skilled in the art.

The objects and advantages of this invention are achieved by the method and implement of this invention.

In accordance with this invention, the disadvantages of the prior art are avoided, actually undamaged, unchanged and representative samples can be taken and evaluated, and damage to the sampling area be avoided, are achieved in a technologically very advanced manner. A sampler is used which consists entirely, or at least at its surface or contact area, of a plastic material which is soluble in water. The sampler, after wetting and hence superficial dissolution, is brought into contact with the surface to be examiner, so that sample material sticks to the plastic material. The sampler is removed and dissolved for collection of the sample material.

The method (and implement) of this invention is used primarily for diagnostic or scientific examinations in biology, medicine or engineering. The sample taken can include samples of bacteria and other microorganisms, of cellular materials and of other very small particles of organic or inorganic materials.

In an advantageous embodiment of this invention applicable in particular the microbiology, for sanitary examinations and similar purposes, the sampler or at least the part of the sampler consisting of the water-soluble plastic is introduced after sampling directly into a culture and nutrient medium. The plastic is dissolved in such medium so that the microorganisms are free to grow and can be examined.

In another embodiment of this invention, the sampler (after sampling) is placed with its contact area on a microscopic slide or is spread out on a slide. Then the plastic is carefully dissolved on the slide by the addition of water. During dissolution of the plastic, the individual constituents of the sample, i.e., the individual microorganisms, cells, particles, etc., adhere to the slide at the same place where they are deposited when the sampler is placed on the slide. Thus the original topography of the area to be examined is represented unchanged as an imprint on the slide. Any diagnostic staining method, without reservations, can now be used to stain the sample prepared in this way.

In addition, according to this invention, e.g., when examining cells by the above-described imprint method, the sample material can simultaneously be fixed by adding alcohol to the water which is used to dissolve the plastic material on the microscopic slide.

The implement or instrument used to carry out the method of this invention, i.e., the sampler, should preferably consist of a water-soluble plastic material which is a polyvinyl alcohol or a polyvinyl pyrrolidone.

The sampler of this invention can be in the form of a sheet or consists of a carrier which is coated with the water-soluble plastic material. In the latter case it is possible, for example, to cut open the plastic coating after sampling and to spread it out on the microscopic slide, or e.g., if microorganisms are to be investigated, to introduce it into the culture and nutrient medium.

A special advantage of the method of this invention and of the relevant sampler is that sufficiently large samples can be taken from both large and extremely small surfaces, without any damages being done to the sample material or the area examined.

The materials required for carrying out the method of this invention, in particular the plastic which is soluble in water, are extremely cheap to produce and shape. Plastic film made from a material of this type may be so thin and pliant that it can be fitted without any gap and also to uneven surfaces.

Other characteristics, advantages and potential applications of this invention are obvious from the following description of further details and embodiments of this invention.

DETAILED DESCRIPTION OF THIS INVENTION

Collection of cells, microorganisms and the like in diagnostic examinations and for scientific work in biology and medicine may be carried out, for example, as follows:

Prior to sampling, a sheet of water-soluble plastic material is partially dissolved by briefly wetting with water. This is not necessary if, for example, the moisture content of an organ or tissue surface to be examined is sufficiently high. The now-sticky surface of the sampler is placed on the surface to be examined and brought into contact with it by applying slight pressure. After having been pulled off, the thin, soft and pliant plastic film used in this case is placed with its contact surface and the adhering sample material onto a microscopic slide. Preferably the microscopic slide consists of glass. The sample material is spread out on the slide by application of slight pressure.

Subsequently, the slide is introduced into a vessel containing pure water or an alcohol-water mixture. The film dissolves, and the alcohol in the water, at the same time, leads to fixation of the collected sample material. After complete dissolution of the film, the collected sample adheres to the glass surface of the slide. Its full topography is retained. Further treatment and examination is done using conventional procedure as used in histology (staining).

In a similar manner, microorganisms and other particles are collected from surfaces to be examined and deposited onto glass slides according to the above-described method of preparation, their local distribution being retained.

For collecting cells or microorganisms from difficulty accessible orifices and cavities of the body, such as, the uretha or tear duct, the sampler according to this invention is adapted in size and shape to the sampling area. For example, the plastic sheet can be applied onto a carrier stick. The plastic sheet is cut open after sampling, and then spread out on the microscopic slide.

In other cases it is useful to coat the sampling instrument, e.g., the surface of a probe stem, whose diameter corresponds to that of the urethra, with the water-soluble plastic material by the dip tank method. A conventional applicator is then used to introduce the superficially moistened, coated probe into the urethra and to bring the surface of the urethra into contact with the probe. After a short period of time the urethra is dilated and the probe is removed. Subsequently, the contact surface of the plastic coating of the probe is applied in the longitudinal direction to a microscopic slide, and the plastic is dissolved.

For other applications in biology and medicine, e.g., for gynaecological medical checkups, it is expedient for example to use a stamp-like sampler consisting of a foam plastic as a carrier for the water-soluble polymer coating. After sampling, the plastic sheet is removed from the carrier, and the imprint thus obtained is transferred to a microscopic slide. In his way, a direct and comparative assignment of the microscopic image to the microscopic findings is achieved.

All samples collected and prepared on microscopic slides according to the method of this invention can be evaluated very easily by a rapid microscopic process using phase-contrast optics, in addition to the conventional preparation and staining processes customary in microscopic diagnostics. According to this invention, the plastic sheet with the adhering sample material which has been placed on the microscopic slide is only partly dissolved with water and then immediately covered with a cover glass.

The resultant preparation can be immediately examined under the microscope, without any loss in optical quality, and thus is durably embedded.

When using the method of this invention for examining microorganisms, it was found that when the water-soluble plastics is a polyvinyl alcohol and a polyvinyl pyrrolidones, the water-soluble plastic does not have a negative effect on the growth of bacteria in the nutrient medium. Also, detrimental side effects of a different nature were not observed.

The samples used for this application either had the form of sheets or films or were produced by the dip tank method, or were coated with the water-soluble plastic material. There is almost unlimited choice as regards the carrier material and its shape. After sampling, the coating made of the water-soluble plastic material is for example, cut open, scraped off or separated from the carrier in any other suitable way.

Production of a polymer solution for coating the sampler of this invention or production of a sheet or film serving as carrier for water-soluble plastic material may be achieved, e.g., by the following process:

300 parts by weight of polyvinyl alcohol (88 mole percent hydroxyl groups, viscosity 4 cp, according to DIN 53015) are dissolved in 120 parts by weight of glycerol p.A., 400 parts by weight of ethyl alcohol p.A. and 440 parts by weight of distilled water.

To coat the carrier, the sampler is immersed in this solution, then removed from the solution and the resultant film is left to dry.

Plastic sheet or film suited to produce samplers is produced either by conventional casting or by spread-coating or knife-coating of the solution in a thin layer onto a plastic substrate which is inert to the solution and from which it can be removed after drying. For carrying out the method according to this invention, coating or film thickness of 0.1 mm have been found to be particularly favorable.

The method of this invention can also be used for an application other than those described above. For example, it is possible in general to use the film imprint method of this invention not only for collecting microorganisms from sanitary equipment and determining them in an overall quantitative way, but their evaluation can also be effected selectively in order to determine their distribution in a specific area.

The method of this invention means substantial technological progress in the following fields of application:
- Germ detection in the food industry
- Detection of fungi and microrganisms in plants and parts of plants
- Soil sampling
- Collection of organic substances, textile fibers and other small particles in criminal investigations

What is claimed is:

1. A method for taking and collecting sample material characterized in bringing a sampler, after wetting and hence superficial dissolution, said sampler consists entirely, or at least at its surface or contact area, of a plastic material which is soluble in water, into contact with the surface to be examined, whereby said sample material sticks to the plastic, removing said sampler from contact with said surface, placing said sampler, or at least said surface or contact area of said sampler, after sampling, on a microscopic slide, or spreading it out on a slide, and dissolving said plastic material carefully on said slide by the addition of water, during such process the individual constitutents of said sample material adhering to said slide at the respective contact sites with retention of the original topography of the sampling area.

2. A method as claimed in claim 1 wherein alcohol is admixed to the water by which said plastic material on the microscopic slide is dissolved, whereby, simultaneously with dissolution, fixation of the sample material occurs.

3. A method as claimed in claim 1 wherein said water-soluble plastic material is selected from the group which consists of polyvinyl alcohol and polyvinyl pyrrolidone, and is in the form of a film or sheet.

4. A method for taking and collecting sample material characterized in bringing a sampler, after wetting and hence superficial dissolution, said sampler consisting entirely, or at least its surface or contact area, of a plastic material which is soluble in water, and said water-soluble plastic material being in the shape of a film or sheet, into contact with the surface to be examined, whereby said sample material sticks to the plastic, and removing and dissolving said sampler, whereby said sample material is collected with the original topography of the sampling area being retained.

5. A method as claimed in claim 4 wherein said sampler or at least the part of said sampler consisting of the water-soluble plastic material is introduced into a culture and nutrient medium after sampling.

6. A method as claimed in claim 4 wherein said water-soluble plastic material is selected from the group which consists of polyvinyl alcohol and polyvinyl pyrrolidone.

7. A method as claimed in claim 4 wherein said taking and collecting of sample material is for scientific or diagnostic examination.

8. A sampler for taking and collecting sample material, particularly for scientific and diagnostic examinations, characterized in that said sampler consists entirely of, or at least at its sample-taking surface or contact area, of a plastic material which is soluble in water, said water-soluble plastic material being in the shape of a film or sheet, said sampler allowing the sample material to be collected to retain the original topography of the sampling area.

9. A sampler as claimed in claim 8 wherein said water-soluble plastic material is selected from the group consisting of polyvinyl alcohol and polyvinyl pyrrolidone.

10. A sampler as claimed in claim 9 wherein said sampler consists of a carrier which is coated with the water-soluble material.

* * * * *